US006828139B2

(12) United States Patent
Schmidt et al.

(10) Patent No.: US 6,828,139 B2
(45) Date of Patent: Dec. 7, 2004

(54) PRODUCTION OF REPLICATIVE HEPATITIS C VIRUS

(75) Inventors: Emmett Vance Schmidt, Andover, MA (US); Raymond Taeyong Chung, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 10/205,962

(22) Filed: Jul. 26, 2002

(65) Prior Publication Data

US 2003/0013085 A1 Jan. 16, 2003

Related U.S. Application Data

(62) Division of application No. 09/597,767, filed on Jun. 20, 2000, now Pat. No. 6,447,994.
(51) Int. Cl.$^7$ .......................... C12N 7/00; C12N 15/85; C12N 15/86; C07H 21/04; C12P 19/34
(52) U.S. Cl. ................ 435/235.1; 435/91.1; 435/91.31; 435/91.21; 435/41; 435/42; 435/440; 435/320.1; 435/325; 435/5; 435/6; 424/225.1; 424/228.1; 536/24.5
(58) Field of Search ............................... 425/5, 6, 7.21, 425/465, 366, 91.1, 91.33, 91.4, 325; 424/9.1, 228.1

(56) References Cited

FOREIGN PATENT DOCUMENTS

WO    WO 98/39031    9/1998

OTHER PUBLICATIONS

He et al., "Successful, Inhibitable HCV RNA Replication in Mammalian Cells Using a Novel Expression System," Antiviral Therapy, 5 (Suppl. 1):49, Apr. 2000.
Chung et al., "Successful Synthesis of Negative Strand HCV RNA in Mammalian Cells Using a Binary Expression System" Hepatology, 30:354A, 1999.
Saquib et al., "Hepatitis C Virus Negative Strand Synthesis in Mammalian Cell Culture Using a Novel Binary Expression System." Pediatric Research 47:276A, Apr. 2000.
Chung et al., "Interferon Alfa but not Ribavirin Directly Inhibits HCV RNA and Protein Synthesis in a Novel Cell–Based Replication System," Hepatology, 32:226A, Oct. 2000.
He et al., "Interferon Exerts Dose–Dependent Selective Inhibitory Effects on HCV Internal Ribosome Entry Site–Mediated Translation in a Novel Replication System," Hepatology, 34:357A, 2001.
Chung et al., "Hepatitis C Virus Replicaiton is Directly Inhibited by IFN–α in a Full–Length Binary Expression System," Proceedings of the National Academy of Sciences USA, 98:9847–52, 2001.
Contreras et al., "Quasispecies Generation in a Novel HCV RNA Replication System is a Region–Specific and Increased by Addition of Ribavirin," Hepatology, 24:413A, 2001.
Hiasa et al., "Sustained HCV Replication in a Cell–Based HCV Replication System Using Replication–Defective Adenoviral Vectors," Hepatology, 36:204A, 2002.
Schmidt et al., "RNA Viral Mutations are Region–Specific and Increased by Ribavirin in a Novel Hepatitis C Replicaiton System," Pediatric Research, 51:263A–264A, 2002.
Contreras et al., "Viral RNA Mutations are Region Specific and Increased by Ribavirin in a Full–Length Hepatits C Virus Replication System" Journal of Virology, 76:8505–8517, 2002.
He et al., "Successful, Inhibitable HCV . . . ," Hepatology, 30:102A, 1999.
Houghton, Michael, "Hepatitis C Viruses," Fields Virology, 3rd Edition, Chap. 32, pp. 1035–1058, 1996.
Filocamo et al., "Selection of Functional . . . ," Journal of Virology, 73:561–575, 1999.
Aoki et al., "A Human Liver Cell . . . ," Virology, 250:140–150, 1998.
Agapov et al. Use of the vaccinia virus/T7 expression system for studying HCV protein processing, in Methods Molecular Medicine; Hepatitis C protocols, edited by Lau et al. 1998, vol. 19, pp. 303–304.

*Primary Examiner*—James Housel
*Assistant Examiner*—Bao Qun Li
(74) *Attorney, Agent, or Firm*—Fish & Richardson P.C.

(57) ABSTRACT

A nucleic acid having a first nucleotide sequence encoding an infectious hepatitis C virus, a second nucleotide sequence encoding a ribozyme, and an inducible promoter operably linked to the first and second nucleotide sequences, the ribozyme being configured to remove a 3' sequence unnecessary for replication of the infectious hepatitis C virus from a transcript initiated by the inducible, is described. A cell containing the nucleic acid and methods of using the cell are also described.

7 Claims, 2 Drawing Sheets

SEQUENCE LISTING

<160> NUMBER OF SEQ ID NOS: 2

<210> SEQ ID NO 1
<211> LENGTH: 36
<212> TYPE: DNA
<213> ORGANISM: Artificial Sequence
<220> FEATURE:
<223> OTHER INFORMATION: Oligonucleotide sense primer

```
<400> SEQUENCE: 1
ccgtcgtttt acaacgtcgt gactgggaaa accctg                    36

<210> SEQ ID NO 2
<211> LENGTH: 34
<212> TYPE: DNA
<213> ORGANISM: Artificial Sequence
<220> FEATURE:
<223> OTHER INFORMATION: Oligonucleotide antisense primer

<400> SEQUENCE: 2
tatacgactc actataggcc attcgccatt cagg                      34
```

PRODUCTION OF REPLICATIVE HEPATITIS C VIRUS

Figure 1:
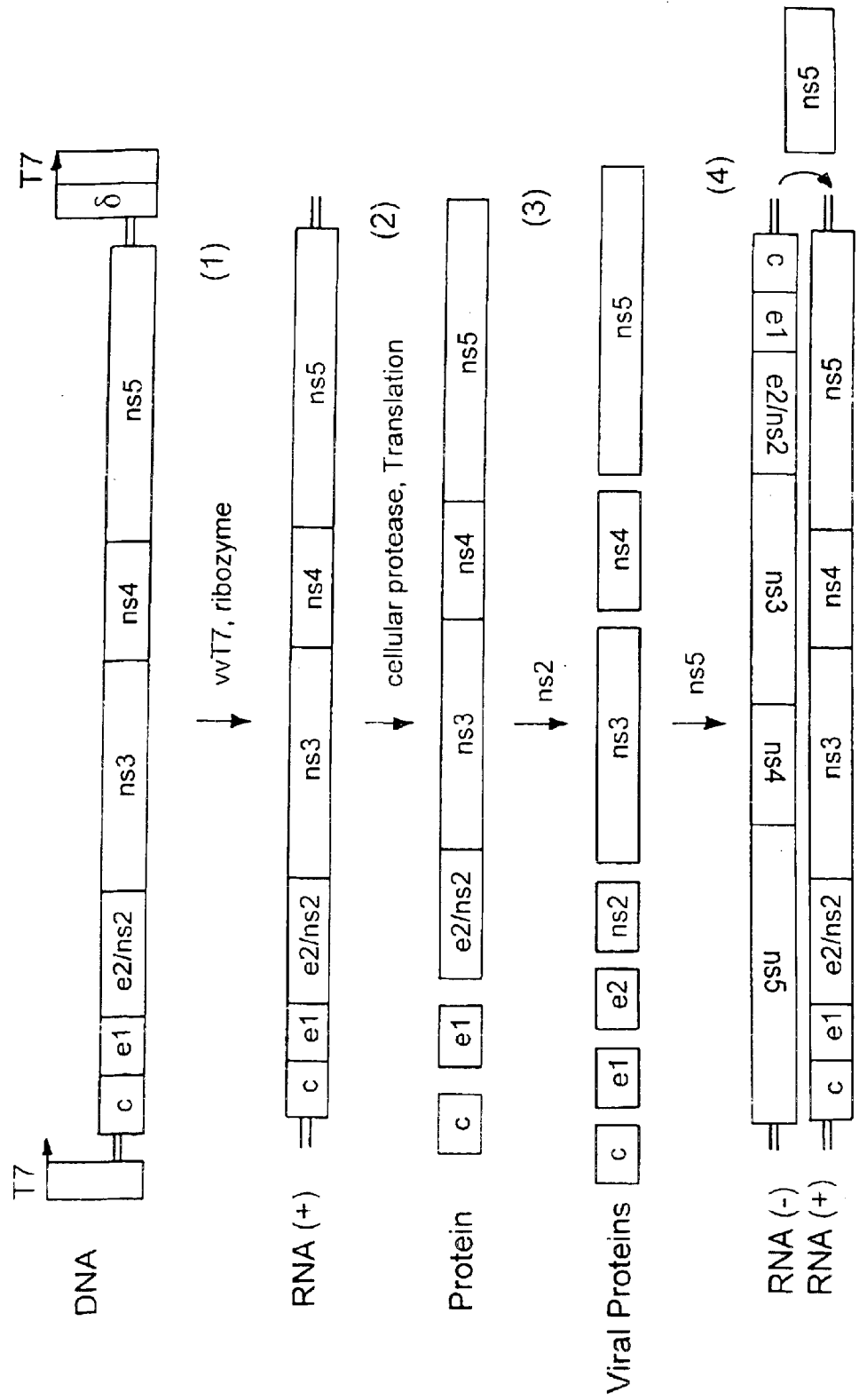

This application is a divisional of U.S. application Ser. No. 09/597,767, filed Jun. 20, 2000 now U.S. Pat. No. 6,447,994.

STATEMENT AS TO FEDERALLY SPONSORED RESEARCH

This invention was made with Government support under National Institutes of Health grants RO1 DK57857-01 and RO1 AI43478-02. The Government has certain rights in the invention.

FIELD OF THE INVENTION

The invention relates to virology and antiviral drug screening.

BACKGROUND OF THE INVENTION

The development of anti-viral strategies against hepatitis C virus (HCV) infection has been hindered by the lack of an ideal animal model, or even a cell culture system, for HCV replication. One characteristic of an ideal HCV animal model or cell culture system would be the ability to induce expression of an infectious HCV in a cell in vitro or in vivo.

The HCV genome consists of a positive strand RNA that encodes a single precursor viral protein that is cleaved by cellular and viral proteases to generate viral structural and non-structural proteins, respectively. Non-translated regions 5' and 3' (5'NTR and 3'NTR) to the open reading frame encoding the precursor protein are also involved in viral replication. For a review of HCV, see Houghton, "Chapter 32, Hepatitis C Viruses," in: Fields Virology, 3rd ed., Fields et al. eds., pp 1035–1058, 1996, Lippincott-Raven Publishers, Philadelphia, Pa.

Infection with HCV is one of the leading causes of chronic liver disease throughout the world. Chronic infection nearly always ensues after acute exposure to HCV, and chronically infected individuals develop cirrhosis and hepatocellular carcinoma at a dramatically elevated rate compared with the rate of disease in an uninfected population.

The development of more effective treatments has been limited by the lack of an effective tissue culture or small animal model of infection. HCV replication systems based on a self-replicating HCV RNA replicon is dependent only on expression of the nonstructural viral proteins. Therefore, such systems do not recapitulate all steps of the HCV virus life cycle, some of which may be effective targets for antiviral intervention. Cell lines stably transfected with the HCV precursor are not capable of HCV RNA replication. Consequently, such cell lines cannot be used to screen for antiviral drugs that block viral RNA replication. RNA transcripts from an infectious HCV cDNA clone can replicate in chimpanzees, but any model that requires the use of large, expensive primates is impractical.

SUMMARY OF THE INVENTION

To address the historical and intractable limitations in the above HCV replication models, the invention provides an inducible system for producing infectious or replicative HCV, as described in the Example below, thereby fulfilling a long-felt need for an ideal HCV replication system.

The invention is based on the development and implementation of an inducible cell-based system for producing replicative HCV. Because the HCV produced by this system is replicative and has the full complement of genetic material found in HCV (e.g., naturally occurring HCV), all aspects of the HCV life cycle can be examined, e.g., in screening assays for candidate antiviral compounds. The inducibility of the system allows the propagation of cells or animals containing HCV genetic material without the damaging effects of HCV replication. Thus, viral replication is induced only when desired, for example, in a particular step that requires infectious HCV replication in an assay.

Accordingly, the invention features a nucleic acid having a first nucleotide sequence encoding an infectious hepatitis C virus, a second nucleotide sequence encoding a ribozyme (e.g., a hepatitis D virus ribozyme), an inducible promoter (e.g., a T7 promoter) operably linked to the first and second nucleotide sequences, and optionally a transcription termination signal (e.g., a T7 transcription termination signal) operably linked to the first and second nucleotide sequences, the ribozyme being configured to remove a 3' sequence unnecessary for replication of the infectious hepatitis C virus from a transcript initiated by the inducible promoter and optionally terminated by the transcription termination signal. The invention also includes cells that harbor a nucleic acid of the invention.

A method of producing infectious HCV is also included in the invention. A cell containing the nucleic acid of the invention (e.g., as an episome or an integrated cassette) can then be used to generate infectious HCV by inducing the inducible promoter of the nucleic acid. For example, if the promoter is a T7 bacteriophage promoter, HCV is produced by expressing a T7 RNA polymerase in the cell. The T7 RNA polymerase in turn can be expressed by infecting the cell with a viral vector (e.g., a vaccinia vector) encoding the T7 RNA polymerase. Alternatively, the cell can contain an episomal plasmid or genomic transgene (e.g., delivered by a retrovirus) that expresses T7 RNA polymerase. Regardless of the vectors used to express T7 RNA polymerase, the expression of the polymerase can itself be regulated, depending on the genetic elements operably linked to the sequence encoding the polymerase.

The invention further includes a screening method for identifying a compound (e.g., a polypeptide, small molecule, or nucleic acid, such as an antisense nucleic acid or ribozyme) that inhibits replication of an HCV. The method includes (1) providing a test cell containing a nucleic acid of the invention, (2) inducing the inducible promoter of the nucleic acid, (3) contacting the test cell with a candidate compound, and (3) detecting a decrease in the amount of infectious hepatitis C virus produced by the test cell compared to the amount of the infectious hepatitis C virus produced by a control cell. The detecting step can include measuring (e.g., by PCR) the amount of negative strand hepatitis C viral RNA in the cell or the amount of positive strand hepatitis C viral RNA in the cell or in cell-free virions produced by the cell.

Since it is possible that the candidate compound inhibits HCV replication by inhibiting a viral or cellular protease responsible for cleaving the HCV precursor protein, the screening method can further include determining whether a hepatitis C virus structural or non-structural protein is cleaved from a hepatitis C virus precursor protein in the cell after the contacting step, e.g., by protein gel electrophoresis.

As used herein, "inhibits" or "inhibition" means any measurable decrease (e.g., 10%, 20%, 50%, 90%, or 100%) in an activity of interest.

As used herein, an "infectious hepatitis C virus" means an HCV that is capable of propagation in a population of cells in vivo or in vitro. Therefore, an infectious hepatitis C virus minimally contains (1) a sequence encoding a precursor protein and (2) 5' and 3' non-translated flanking sequences sufficient to support virus replication (i.e., each step of the virus life cycle) in a cell population.

By one genetic element being "operably linked" to another is meant that a genetic element (either in a plus strand, minus strand, or double stranded form) is structurally configured to operate or affect another genetic element. For example, a promoter operably linked to a sequence encoding a polypeptide means that the promoter initiates transcription of a nucleic acid encoding the polypeptide, and a transcription termination signal operably linked to the sequence encoding the polypeptide means that the transcription termination signal terminates transcription of a nucleic acid encoding the polypeptide.

The nucleic acids and methods of the invention provide a HCV replication system amenable to comprehensive, yet relatively inexpensive (as compared to infection of a primate), antiviral drug screening methods. Because the HCV replication system performs all steps of the virus life cycle, candidate antiviral compounds can be screened for activity against any vital viral or cellular drug target involved in virus replication. In addition, the HCV replication system is inducible, thereby allowing cells to vigorously replicate in the absence of HCV until virus replication becomes necessary for the particular step of a screening assay performed. Thus, the nucleic acids and methods of the invention remove a substantial obstacle in anti-HCV drug development.

Other features or advantages of the present invention will be apparent from the following detailed description, and also from the claims.

BRIEF DESCRIPTION OF THE DRAWING

FIG. 1 is a schematic diagram of the infectious HCV production system described herein. "δ" is the hepatitis D ribozyme. "T7" above the box, on the left side of the schematic diagram for "DNA" is the T7 promoter. "T7" above the box, on the right side of the schematic diagram for "DNA" is the T7 transcription termination signal. "vvT7" is the vaccinia virus vector encoding the T7 RNA polymerase.

FIG. 2 is a schematic diagram of a non-infectious control DNA construct and of the positive strand RNA produced from it.

DETAILED DESCRIPTION

The nucleic acid, such as an expression plasmid, of the invention can be constructed using standard methods and reagents in the art of molecular biology. For example, inducible promoters, such as the T7 promoter system (Aoki et al., Virology 250:140–150, 1998; WO 98/39031) can be used to provide controlled expression of the infectious HCV clone. Alternatively, a tetracycline-inducible promoter system can be used (Moradpour et al., Hepatology 28:192–201, 1998). The inducible promoter is then operably linked to an infectious clone of an HCV, such as the one described in Yanagi et al., Proc. Natl. Acad. Sci. USA 94:8738–8743, 1997; or Kolykhalov et al., Science 277:570–574, 1997. At the 3' end of the HCV clone, a ribozyme (e.g., a hepatitis D virus ribozyme) and optionally a transcription termination signal (e.g., a T7 transcription termination signal) is attached. Ideally, a cis-acting ribozyme, such as a HDV ribozyme, that cleaves at the boundary with the 3' terminus of the HCV RNA is suitable for this purpose. After the HCV clone is transcribed, the ribozyme serves to remove itself and other 3' sequences which may hinder virus replication.

Depending on the inducible promoter used to drive transcription of the infectious HCV clone, the method for inducing HCV production will vary. For example, if a T7 promoter is used, then transcription is induced by expressing a T7 RNA polymerase in a cell harboring the nucleic acid (e.g., as a result of transfection, viral vector delivery, or genomic DNA integration). The polymerase can be expressed using a viral vector, such as the vaccinia vector described in the Example below, or the adenovirus vector described in Aoki et al., supra. Alternatively, a T7 polymerase expression vector under the control of a mammalian promoter can be introduced into the cell to induce HCV production. In addition, the cell can already contain a stably integrated expression cassette that is induced to express T7 polymerase, thereby producing replicative HCV.

To allow propagation of HCV, induced cells are optionally mixed with a population of cells that do not produce HCV but are permissive for HCV infection. A mixed or unmixed population can then be used in screening assays for candidate antiviral compounds. Depending on the nature of a candidate compound, contacting the population of cells with the compound can involve a variety of standard techniques. If the candidate compound is a small molecule drug that can pass through lipid membranes, all that is needed for the contacting step is the addition of the compound to an aqueous mixture containing the cells. However, if the compound is a protein or nucleic acid intended to elicit its antiviral effect inside a cell, the contacting step may require other techniques. A protein compound can be delivered into the cell by encapsulation in liposomes or fusion to a viral protein that is delivered inside a cell by viral infection. A nucleic acid can be delivered into the cell using a viral vector or a transfection protocol (e.g., electroporation). Methods of introducing proteins and nucleic acids into a cell are well known in the art of molecular biology.

After the contacting step, the amount of infectious hepatitis C virus produced in the presence of the compound is measured and compared to a control amount of infectious hepatitis C virus. The control amount is generally an amount observed in a similar population of cells grown in the absence of the candidate compound.

The amount of HCV can be measured using any suitable direct or indirect method. Several suitable methods are known in the art. For example, the amount of positive strand viral RNA in cells and in virions can be measured using quantitative PCR. The amount of minus strand RNA can also be measured using PCR. In addition, viral proteins, rather than viral nucleic acids, can be measured, e.g., in the supernatant of an HCV-infected cell culture, using an enzyme linked immunosorbent assay (ELISA). Such assays typically utilize monoclonal or polyclonal antibodies to capture viral antigens in a sample. The captured antigens are then detected using labeled antibodies that specifically bind to the captured antigen at an epitope different from the one to which the capture antibody binds. HCV enzyme-linked immunoassays are available from Abbott Laboratories. In addition, any decrease in the level of cleavage of the viral precursor protein caused by the presence of the candidate compound provides information regarding the mode of action of the compound. For example, decreased cleavage could lead to asking whether the compound binds and inhibits a viral or cellular protease. Thus, an examination of the level of precursor protein cleavage can be a valuable step in the screening methods of the invention.

The methods of the invention can be performed repetitively and in parallel to screen libraries of compounds (e.g., a small molecule library, a peptide library, or a single chain antibody library) for candidate antiviral drugs. For example, cells having a nucleic acid of the invention can be cultured in the wells of a 96-well microtiter plate. Before or after induction of HCV replication, each member of the compound library is deposited into one well, and the level of HCV replication determined in the well. Thus, automation of the methods of the invention are especially amenable to high throughput screening of chemical libraries.

This invention can also be used to identify key cellular proteins involved in HCV RNA replication by identifying replication complexes, and to identify host cellular genes that are induced by expression of replicative HCV.

One skilled in the art can, based on the above disclosure and the example described below, utilize the present invention to its fullest extent. The following example is to be construed as merely illustrative of how one skilled in the art can make and use the inducible HCV replication system described herein. Any publications cited in this disclosure are hereby incorporated by reference.

EXAMPLE

Materials and Methods

Preparation of constructs. The HCV construct originally used to generate infectious transcripts was the H77 clone (Yanagi et al., Proc. Natl. Acad. Sci. USA 94:8738–8743, 1997). The plasmid containing the clone, pCV-H77, contains the full-length genotype 1a HCV sequence of strain H77. The plasmid contains a T7 promoter immediately upstream of the viral cDNA and was adapted at its immediate 3' terminus with the hepatitis delta virus cis-acting ribozyme (Wang et al., Nature 323:508–514, 1986) in continuity with the T7 terminator sequence. To accomplish this, a synthetic antisense oligonucleotide was made, the oligonucleotide being the complement of the following contiguous sequences: the terminal 3' 20 nucleotides of the H77 strain, followed immediately by the 85-nucleotide HDV ribozyme, followed immediately by the 48-nucleotide T7 terminator. This 153-nucleotide sequence was divided into two overlapping 85-nucleotide primers, each sharing 17 nucleotides in common. These primers were synthesized (IDT, Coralville, Iowa) and used as the downstream primers in a series of PCR reactions.

A sense oligonucleotide of 85 nucleotides in length, corresponding to HCV H77 sequences 9367–9451, was also synthesized in a similar manner. H77 numberings, as use herein, are as designated in Yanagi et al., supra. The sense primer and the inner antisense primer were used in a PCR reaction with 10 ng of pCV-H77 as a template under the following conditions: 50 pmol of primer, 0.5 U Taq polymerase, 1.5 mM $MgCl_2$, 0.5 $\mu$M each dNTP. The 100 $\mu$l reaction was carried out with 20 cycles of PCR under the following cycling conditions: 95° C. for 1 minute, 65° C. for 1 minute, and 72° C. for 1 minute. The PCR product was gel purified (QIAquick, QIAgen, Chatsworth, Calif.) and cloned into the vector pcDNA3.1/V5/His-TOPO (Invitrogen, Carlsbad, Calif.). This product then served as the template for a second PCR reaction under identical conditions using the sense primer and the outer antisense primer. The product of the second amplification was again cloned into pcDNA3.1/V5/His-TOPO to generate pHCV-Rz-TOPO. The sequence of this product was confirmed bi-directionally by dideoxy sequencing.

Because the parent plasmid for pCV-H77C, pGEM-9z, contained a second T7 promoter at its original multiple cloning site just downstream of the HCV cDNA, this sequence was removed by excising the XbaI-SfiI fragment. A synthetic XbaI-MluI-MluI-SfiI linker pair was generated, and ligated into the XbaI-SfiI-digested pCV-H77C. Successful insertion of a single linker was confirmed by sequencing. This product, pCV-H77C-Mlu, was digested with AflII and MluI, and the AflII-MluI fragment isolated from pHCV-Rz-TOPO was subcloned into this vector, to yield pT7-flHCV-Rz. Successful insertion of HDV Rz and T7 terminator sequences was confirmed by bi-directional sequencing.

Figure 2:
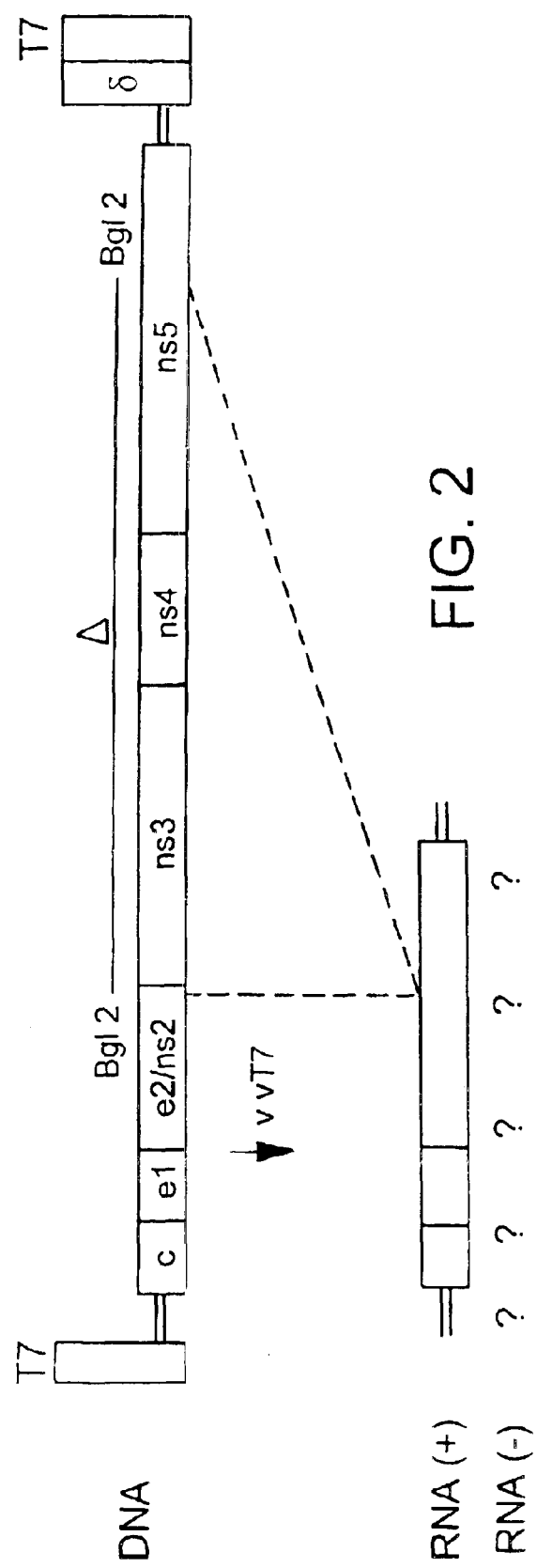

To confirm the dependence of the replication system on intact HCV non-structural proteins, which had been postulated to be essential for RNA replication, a deletion mutant was produced by removing the BglII-BglII fragment from pT7-flHCV-Rz (FIG. 2). The deletion spanned HCV nucleotides 3237–8939. This deletion removed the downstream portion of NS2 to NS5B, inclusive of the active site motif of the NS5B RNA-dependent RNA polymerase. The 5.7 kb deletion was predicted to keep the polyprotein in frame. The deletion was confirmed by sequencing of pT7-HCVD BglII-Rz. For experiments designed to examine vaccinia-T7 efficiency, the positive control plasmid OS8 contained a T7 promoter flanking the β-galactosidase gene.

Cell lines. Cells were maintained in DMEM (BRL Gibco, Rockville, Md.) containing penicillin (50 IU/mL) and streptomycin (50 $\mu$g/mL) and was supplemented with 10% fetal calf serum. CV-1 cells were obtained from the American Type Culture Collection. For some experiments, HepG2 and Huh7 cell lines were used for transfection/infection.

Transfection/infection experiments. Expression of HCV was carried out using an adaptation of the binary expression system described in Fuerst et al., Proc. Natl. Acad. Sci. USA 83:8122–8126, 1986. Subconfluent CV-1 cells, chosen because of their enhanced transfection efficiency, were transfected in 6-cm tissue culture plates using 1 $\mu$g of plasmid (pT7-flHCV-Rz, pT7-HCVDBglII-Rz, OS8) with 3 $\mu$l of Lipofectamine transfection reagent (GIBCO BRL) in serum-free DMEM. Following 4 hours of transfection, the cells were washed and replaced with DMEM containing 10% FCS. Twenty-four hours post-transfection, recombinant vaccinia-T7 polymerase (vTF7-3; Fuerst et al., supra) was added to the cells at an MOI of 10. Twenty-four hours post-vTF7-3 infection, cells were lysed and analyzed for RNA and protein expression. The positive control vector OS8 verified successful T7 polymerase expression.

Strand-specific RT-PCR. To confirm successful HCV RNA strand synthesis, strand-specific RT-PCR was carried out on lysates of transfected/infected cells. RNA was extracted using TRIzol reagent (GIBCO BRL), and subjected to two rounds of DNase I digestion (5 U, Boehringer Mannheim, Indianapolis, Ind.) at 37° C. for 60 minutes. The RNA was then phenol/chloroform-extracted and resuspended in DEPC-treated water. The purified RNA was then subjected to strand-specific RT-PCR using primers corresponding to the 5' and 3' genomic and antigenomic H77 RNA. The following oligonucleotide sequences, all 20-mers, were used: 5' end sense, H77 nt 29–48; 5' end antisense, nt 390–371; 3' end sense, nt 9241–9260; and 3' end antisense, nt 9361–9342. For detection of genomic (+) strand RNA, the antisense primer was used for the reverse transcription step. For detection of antigenomic (−) strand RNA, the sense primer was used for the reverse transcription step. Reverse transcription was carried out in 20 $\mu$l reactions with the following components: 1 $\mu$l RNA, 25 pmol RT primer, 0.5 U AMV reverse transcriptase (Perkin Elmer, Branchburg, N.J.), 1.5 mM $MgCl_2$, 0.5 $\mu$M each dNTP, and 1U RNasin (Perkin Elmer). The reaction was carried out at 42° C. for 15 minutes, and the enzyme was heat inactivated for 10 minutes at 99° C. The resulting product was treated with three successive rounds of DNase I (Boehringer Mannheim) at 37° C. for 30 minutes each, and the final product was purified by phenol/chloroform extraction. The cDNA was then subjected to 25 cycles of PCR using 25 pmol each of the relevant sense and antisense primers, 0.5 µM each dNTP, 1.5 mM MgCl$_2$, and 0.5 U Taq polymerase. Reaction products were then analyzed by 1.6% agarose gel electrophoresis.

Ribonuclease protection assay (RPA). To confirm HCV replicative RNA synthesis by a second line of investigation, RPA was performed on the extracted RNAs. A probe was used for specific detection of antigenomic HCV RNA at the 3' terminus of the genome. To accomplish this, the vector pHCV-3'T (Chung et al., Biochem. Biophys. Res. Commun. 254:351–362, 1999) was used to generate a sense probe corresponding to the terminal HCV RNA. This vector contains the highly conserved 98-nucleotide 3' terminal sequence (also conserved in H77) that had been adapted and cloned into the EcoRI and XbaI sites of pSP72. Following linearization of pHCV-3'T by XbaI, an α-$^{32}$P-UTP-labeled probe was generated by in vitro transcription using T7 polymerase according to manufacturer's protocol (Ambion, Houston, Tex.). This probe was purified by phenol/chloroform extraction and then used for RPA. For all RPAs, the RPA II kit was used in accordance to manufacturer's instructions (Ambion). RPA products were separated by 8 M urea/5% PAGE. For the HCV replicative strand, the expected protected fragment size was 210 nucleotides. As a positive control, hybridization was performed with the pT7-flHCV-Rz DNA.

To generate RPA probes for human β-actin and GAPDH, commercially available antisense control DNA templates pTRI-β-actin and pTRI-GAPDH (Ambion) were used. As with the HCV template, in vitro transcription in the presence of α-$^{32}$P-UTP was carried out using T7 RNA polymerase (MAXIscript, Ambion). The probes were phenol/chloroform extracted, purified, and used in RPA experiments conducted according to the manufacturer's instructions (RPA II, Ambion). To generate an antisense RPA probe for the detection of β-galactosidase mRNA, a PCR approach was used in which the antisense primer was adapted upstream with the T7 promoter sequence. Oligonucleotide primers corresponding to the coding sequence of β-galactosidase in the vector OS8 were synthesized as follows. The sense strand was 5'-CCGTCGTTTTACAACGTCGTGACTGGG-AAAACCCTG-3' (SEQ ID NO: 1), and the antisense was 5'-TATACGACTCACTATAGGCCATTCGCCAT TCAGG-3' (SEQ ID NO:2; T7 promoter sequence underlined).

PCR was carried out using 10 ng of OS8 as template under the following conditions: 25 pmol each primer, 0.5 µM each dNTP, 1.5 mM MgCl$_2$, 0.5 U Taq polymerase. Twenty-five cycles were performed under the following conditions: 95° C. for 1 minute, 45° C. for 1 minute, 72° C. for 1 minute. PCR products were separated by agarose gel electrophoresis and gel purified (QIAquick, QIAgen). The purified template DNA was then used for generation of α-$^{32}$P-UTP-labeled antisense probe by in vitro transcription with T7 polymerase (MAXIscript, Ambion). RPA was carried out as described above. For β-actin, GAPDH, and β-galactosidase probes, hybridization was carried out using the original template DNAs as positive controls. For the ribavirin and amantadine studies, a simultaneous RPA using GAPDH probe with HCV (−) strand probe was performed, and the results displayed on the same gel.

Western immunoblotting. Lysates were extracted using Laemmli 2×SDS sample-extraction buffer (Sigma, St. Louis, Mo.). Total protein was quantitated by the Bradford assay. Equal quantities of protein were loaded and separated by 10% SDS-PAGE. Following transfer of the gels to PVDF membranes, Western immunoblotting was carried out using the ECL-Western detection method (Amersham, Piscataway, N.J.). For HCV protein detection, polyclonal antisera were used. The antisera were pooled from HCV-infected patients whose sera were reactive by the recombinant immunoblot assay (RIBA-2, Abbott Labs, Chicago, Ill.) at a dilution of 1:50. Horseradish peroxidase-conjugated rabbit anti-human antibody (Amersham) was used at 1:5000 for detection. Five micrograms of recombinant HCV core protein (Austral Biologicals, San Ramon, Calif.) was used as a positive control. For β-galactosidase detection, monoclonal anti-β-galactosidase (Promega, Madison, Wis.) was used as the primary antibody at a dilution of 1:5000. For β-actin, monoclonal anti-actin antibody (Chemicon, Temecula, Calif.) was used at a dilution of 1:200. For both actin and galactosidase immunoblots, conjugated rabbit anti-mouse (Amersham) antibody at 1:10,000 dilution was used as secondary antibody.

Antiviral inhibitor studies. Purified, recombinant IFN-α-2b (INTRON A, Schering Plough Research Institute, Kenilworth, N.J.) was used at incremental doses of 0, 2000, 6000, or 15,000 units/plate. The drug was added to the media at the conclusion of transfection. Time course experiments indicated that IFN-α-2b's inhibition of vaccinia-T7 polymerase was minimized when IFN-α-2b was given 20 hours prior to the introduction of vTF7-3.

Ribavirin (Schering Plough Research Institute) was given at the doses of 0, 10, 20, 80, 120, 160, and 200 mg/plate were added to the media 20 hours prior to introduction of vTF7-3. These doses were comparable to those achievable at physiologic concentrations and at the highest doses given in excess of those found to cause cellular toxicity (Ilyin et al., Hepatology 27:1687–1694, 1998). The results were unchanged when ribavirin was given 0 and 12 hours before vTF7-3 infection.

Amantadine-HCl (Sigma) was used at doses comparable to pharmacologically achievable concentrations (Shannon et al., Antimicrob. Agents Chemother. 20:769–776, 1981). Doses of 0, 1, 10, and 100 µg/plate were added to the media at 20 hours prior to vTF7-3 infection. Results seen were unchanged when amantadine was given 0 and 12 hours before vTF7-3 infection.

Results

Generation of a binary HCV expression system in mammalian cells. To explore whether the early steps in the HCV lifecycle could be recapitulated using a DNA-based approach, the plasmid pCV-H77 provided a starting point for the genetic manipulations. pCV-H77 contained a full-length genotype 1a sequence, inclusive of the highly conserved 5' and 3' untranslated sequences. pCV-H77 was adapted at its 3' terminus with the cis-acting hepatitis delta ribozyme followed immediately by the T7 transcription termination sequence (FIG. 1). The final construct was designated pT7-flHCV-Rz. Because the upstream end of the viral sequence lied immediately downstream of the T7 promoter, T7 polymerase was expected to generate, by transcription, a full-length viral RNA genome bearing bona fide termini for strand replication.

When CV-1 cells were transfected with pT7-flHCV-Rz and infected with recombinant vaccinia encoding T7 polymerase (vTF7-3), detectable RNA corresponding to the genomic or (+) strand and the antigenomic or (−) strand of the viral genome was detected. Strand-specific RNA synthesis was detected by two lines of investigation: strand-specific RT-PCR and ribonuclease protection assay. As confirmation of full antigenomic strand synthesis, (−) strand RNA sequences corresponding to both the 5' and 3' untranslated portions of the genome (i.e., the 5' and 3' termini of the antigenomic strand) were detected by RT-PCR. Using an RNase protection assay, (−) strand RNA corresponding to the 3' terminus of the genome was also detected. This synthesis was dependent on transfection with HCV sequences (pT7flHCVRz) and infection with vTF7-3, but not dependent on pT7-flHCV-Rz alone or on vTF7-3 combined with an unrelated template. Thus, the replication system succeeded in producing the full complement of viral protein synthesis.

To confirm successful viral protein synthesis, Western blotting was performed using polyclonal antisera directed against genotype 1 HCV infection. Immunoreactive HCV core protein was expressed only in the presence of T7-flHCV-Rz and vaccinia-T7, but not with either alone or in the presence of vTF7-3 and an unrelated expression construct. The successful synthesis of β-galactosidase from a control vector confirmed the validity of our binary expression system for CV-1 cells.

HCV antigenomic strand synthesis is dependent on full-length HCV sequences. To confirm that this specific RNA strand synthesis was dependent on the expression of viral proteins, as was expected, the experiments described above was repeated with an expression construct deleted in the region from NS2-NS5 (FIG. 2). This deleted region contained the NS3 RNA helicase and the key catalytic domains of the NS5B RNA-dependent RNA polymerase. Despite inducible production of HCV core protein, in levels comparable to the full length construct, no detectable (−) strand synthesis was seen by either RT-PCR or RNase protection assay.

In the case of the deletion mutant, the inability to carry out successful (−) strand synthesis in the face of preserved structural protein synthesis and in the presence of an intact RNA template terminus strongly suggested that synthesis of antigenomic RNA requires the presence of HCV nonstructural proteins. The finding of equivalent levels of core protein between the wild-type and mutant constructs suggested that the observed protein synthesis was most likely attributable to the initial effects of polyprotein translation by host ribosomes rather than the result of repeated rounds of viral genome replication.

Interferon-α directly and selectively inhibits HCV RNA and protein synthesis. Having established a successful binary cell-based expression system for (−) strand HCV RNA synthesis, the effects of potentially clinically active antiviral compounds on (−) strand synthesis was next examined. It was known that interferon-α-2b (IFN-α), with or without ribavirin, was the only compound approved for the treatment of chronic HCV infection. Without a replication system for HCV, one could not separate IFN-α's direct antiviral effects from its indirect effects, such as immunomodulatory effects. Therefore, the HCV replication system described herein was used to examine the direct effects of IFN-α on HCV replication.

Recombinant interferon-α-2b was added to the cell culture system used to generate replicative HCV, as described above, at doses predicted to have an antiviral effect in tissue culture. A dose-dependent inhibition of HCV (−) RNA synthesis by IFN-α was found at doses from 2000 to 15,000 units/well, which had no effect on RNA levels of actin and β-galactosidase in the RNase protection assay. When IFN-α's effects on protein synthesis were examined, a dose-responsive inhibition of HCV core protein synthesis by IFN-α was observed. This effect was substantially greater than IFN-α modest effects on β-galactosidase levels. Actin protein synthesis was unaffected. Taken together, these data demonstrated that interferon-α exerted a direct antiviral effect on HCV RNA and protein synthesis.

Neither ribavirin nor amantadine inhibit HCV RNA synthesis. The nucleoside analogue ribavirin was known to be an approved agent, in conjunction with interferon-α, for the treatment of chronic hepatitis C infection. While ribavirin did not appear to be effective against HCV in monotherapy, the drug's antiviral effects could be augmented by IFN (Davis et al., N. Engl. J. Med. 339:1493–1499, 1998; and Hoofnagle et al., J. Hepatol. 31:264–268, 1999). To determine whether this compound had direct anti-HCV activity, ribavirin was tested at doses of 10–200 mg/well. These doses are comparable to, and in excess of, those found at clinically applicable concentrations. No inhibitory effect of ribavirin on HCV (−) RNA synthesis was found.

In some reports, amantadine demonstrated an antiviral effect against several RNA viruses, including HCV. When amantadine was tested at doses (1–100 μg/well) in excess of clinically relevant concentrations, amantadine showed no activity against HCV (−) strand synthesis.

Taken together, neither ribavirin nor amantadine demonstrated direct activity against HCV (−) RNA synthesis, suggesting that any observed effect on the control of in vivo infection may be attributable to an indirect mode of action, e.g., an immunomodulatory mode of action. Further, when combined with the positive results obtained for IFN-α above, the studies described herein demonstrate that the HCV replication model can be used to determine whether candidate antiviral compounds have a direct affect on viral replication.

Other embodiments are within the following claims.

What is claimed is:

1. A method of inducibly producing infectious hepatitis C virus, the method comprising providing a cell containing a nucleic acid comprising a first nucleotide sequence encoding an infectious hepatitis C virus, a second nucleotide sequence encoding a ribozyme, and an inducible promoter operably linked to the first and second nucleotide sequences, the ribozyme being configured to remove a 3'sequence unnecessary for replication of the infectious hepatitis C virus from a transcript initiated by the inducible promoter; and inducing the inducible promoter, thereby producing the infectious hepatitis C virus.

2. The method of claim 1, wherein the inducible promoter is a T7 promoter.

3. The method of claim 2, wherein the inducing step is performed-by expressing a T7 RNA polymerase in the cell.

4. The method of claim 3, wherein the T7 RNA polymerase is expressed in the cell via infection by a viral vector encoding the T7 RNA polymerase.

5. The method of claim 4, wherein the viral vector is a vaccinia viral vector.

6. The method of claim 1, wherein the ribozyme is a hepatitis D virus ribozyme.

7. The method of claim 4, wherein the viral vector is an adenoviral vector.

* * * * *